US006355026B1

(12) United States Patent
Mick

(10) Patent No.: US 6,355,026 B1
(45) Date of Patent: Mar. 12, 2002

(54) CORONARY CATHETERS FOR USE IN A TRANSRADIAL CATHETERIZATION

(76) Inventor: Matthew J. Mick, 4424 North, Lake Dr., Shorewood, WI (US) 53211

( * ) Notice: Subject to any disclaimer, the term of this patent is extended or adjusted under 35 U.S.C. 154(b) by 0 days.

(21) Appl. No.: 09/312,578

(22) Filed: May 14, 1999

Related U.S. Application Data

(62) Division of application No. 08/998,131, filed on Dec. 24, 1997, now Pat. No. 5,916,209.

(51) Int. Cl.$^7$ .............................................. A61M 25/00
(52) U.S. Cl. ....................................... 604/523; 604/532
(58) Field of Search ................................ 604/523, 524, 604/525, 530, 532, 264, 500

(56) References Cited

U.S. PATENT DOCUMENTS

| 4,547,193 A | 10/1985 | Rydell |
| 4,573,476 A | 3/1986 | Ruiz |
| 4,735,620 A | 4/1988 | Ruiz |
| 4,883,058 A | 11/1989 | Ruiz |
| 4,961,731 A | 10/1990 | Bodicky et al. |
| 4,973,306 A | 11/1990 | Ruiz |
| 5,016,640 A | 5/1991 | Ruiz |
| 5,188,619 A | 2/1993 | Myers |
| 5,195,990 A | 3/1993 | Weldon |
| 5,203,776 A | 4/1993 | Durfee |
| 5,215,540 A | 6/1993 | Anderhub |
| 5,231,994 A | 8/1993 | Harmjanz |
| 5,299,574 A | 4/1994 | Bower |
| 5,306,263 A | 4/1994 | Voda |
| 5,322,509 A | 6/1994 | Rickerd |
| 5,389,090 A | 2/1995 | Fischell et al. |
| 5,401,258 A | 3/1995 | Voda |
| 5,403,292 A | 4/1995 | Ju |

(List continued on next page.)

FOREIGN PATENT DOCUMENTS

| DE | 92 15 779.3 | 3/1993 |
| EP | 0728494 A1 | 8/1996 |
| EP | 0728494 A1 | 8/1996 |
| JP | 07308384 | 11/1995 |
| JP | 11-114069 | 4/1999 |
| WO | WO 92/12754 | 8/1992 |
| WO | WO 93/14802 | 8/1993 |
| WO | WO 93/21983 | 11/1993 |
| WO | WO 95/15780 | 6/1995 |
| WO | WO 97/09087 | 3/1997 |

OTHER PUBLICATIONS

Mallinckrodt Medical, Inc., Product Information Brochure, Mallinckrodt® Diagnostic Catheters (1990).
Medi–tech® Boston Scientific Corporation, Product Information brochure, Imager™ Angiographic Catheters (DT 530 10/90/5M).
Campeau, Lucien, "Percutaneous Radial Artery Approach for Coronary Aniography," *Catheterization and Cardiovascular Diagnosis* 16:3–7 (1989).
Allen, Edgar, "Methods of Diagnosis of Chronic Occlusive Arterial Lesions Distal to the Wrist with Illustrative Cases," *Thromboangiitis Obliterans*, pp. 237–244 (1929).

*Primary Examiner*—Manuel Mendez
(74) *Attorney, Agent, or Firm*—Godfrey & Kahn, S.C.

(57) ABSTRACT

Right and left coronary catheters that are designed to be used in a transradial coronary catheterization are provided. The catheters have a proximal end, an extended body portion, and a shaped distal end with two curved portions and a tip. When advanced into the ascending aorta, the curved portions of the distal end cooperate with the aorta to engage and maintain the tip of the catheter within the selected coronary ostium during a coronary procedure. Also provided are methods of inserting the catheters into a right or left coronary artery by a transradial approach, and using the catheters in a diagnostic or interventional procedure to selectively deliver an imaging dye or tool to the coronary artery of interest.

19 Claims, 5 Drawing Sheets

U.S. PATENT DOCUMENTS

| | | |
|---|---|---|
| 5,445,624 A | 8/1995 | Jimenez |
| 5,470,322 A | 11/1995 | Horzewski et al. |
| 5,471,986 A | 12/1995 | Ishimura et al. |
| 5,497,774 A | 3/1996 | Swarta et al. |
| 5,527,274 A | 6/1996 | Zakko |
| 5,531,721 A | 7/1996 | Pepin et al. |
| 5,545,151 A | 8/1996 | O'Connor et al. |
| 5,569,218 A | 10/1996 | Berg |
| 5,584,821 A | 12/1996 | Hobbs et al. |
| 5,599,325 A | 2/1997 | Ju et al. |
| 5,603,704 A | 2/1997 | Brin et al. |
| 5,658,263 A | 8/1997 | Dang et al. |
| 5,690,611 A | 11/1997 | Swartz et al. |
| 5,876,385 A | 3/1999 | Ikari et al. |

FIG_1

FIG_3

FIG_4

CORONARY CATHETERS FOR USE IN A TRANSRADIAL CATHETERIZATION

CROSS REFERENCE TO RELATED APPLICATIONS

This application is a divisional of U.S. patent application Ser. No. 08/998,131, filed Dec. 24, 1997, now U.S. Pat. No. 5,916,209

FIELD OF THE INVENTION

The present invention relates to catheters for selective placement in a right or left coronary artery of a patient by transradial approach.

BACKGROUND OF THE INVENTION

In diagnosing and treating heart diseases caused by occlusion of the coronary arteries, a physician may perform various tests and non-surgical procedures in which a catheter is guided through an artery in the arm or leg and into the selected coronary artery of the heart. Once in place, the catheter is then used for performing diagnostic tests such as a coronary angiography in which a radioimaging material is injected to visualize the arteries, or therapeutic interventions such as a coronary angioplasty, stenting, or atherectomy.

In a femoral catheterization procedure, the catheter is introduced into the aorta via the femoral artery in the leg. A drawback of this procedure is that, after it is completed, the patient must remain flat and immobilized with pressure applied to the wound for an extended period of time of about 4–6 hours to ensure that the bleeding stopped.

With a brachial catheterization, the catheter is introduced via the brachial artery in the arm. With this procedure, the patient can be up and walking within a shorter rest period of only about 1–2 hours. However, the deep location of the artery leads to increased bleeding complications, and thrombosis of the artery can occur. Another disadvantage is that a catheter inserted into the brachial artery undesirably cuts off blood flow into the lower arm, wrist and hand. In addition, the shapes of the distal end of coronary catheters that have been described for insertion using a brachial artery approach, such as those in U.S. Pat. Nos. 5,299,574 (Bower) and 5,471,986 (Ishimura), could be improved to more securely maintain the tip of the catheter engaged within the artery and prevent it from backing out of the coronary ostium when angioplasty equipment is advanced into the artery.

A relatively new technique is a transradial approach in which the catheter is introduced into the aorta via the radial artery in the wrist. The radial artery and the ulnar artery are two small arteries in the wrist that communicate through the palmar arch. Advantageously, insertion of a catheter into the radial artery does not cut off blood flow into the lower arm or hand because the blood can continue to flow through the ulnar artery and palmar arch. This approach also requires a relatively short recovery time of about 10–15 minutes to ensure that bleeding has stopped from the surgical wound. Thus, an advantage of the use of a transradial approach for diagnostic catheterization and intervention over femoral or brachial coronary intervention approaches is the early discharge of the patient into outpatient care, and the cost reductions associated with the early discharge and increased availability of recovery beds. In addition, transradial intervention procedures can be performed in a less complicated setting than is required in a femoral or brachial procedure. However, since this approach for coronary angiography was first described in 1989 by Dr. Lucien Campeau (Cathet. Cardiovasc. Diagn. 16:3–7 (1989)), it has gained acceptance in Europe, but only minimal acceptance in the United States. A barrier to the use of this technique is that existing catheters are not designed for optimal use from the radial artery. Current catheters require excessive manipulation and become easily dislodged during examination or treatment.

Therefore, an object of the invention is to provide a catheter for use in coronary diagnosis and/or treatment that is specifically configured for insertion into a coronary artery via a transradial approach. Another object is to provide a right and left radial catheter having a shape such that, when a force is applied that tends to displace the catheter tip out of the ostium of the artery, such as when advancing equipment and/or injecting a dye through the catheter into the artery, the tip of the catheter will not become dislodged and will remain securely seated in the ostium of the artery until completion of the procedure. Yet another object is to provide catheters that require minimal manipulation to engage the coronary ostium, thereby facilitating the ease of the procedure.

SUMMARY OF THE INVENTION

These and other objects and advantages are achieved in right and left coronary catheters that are designed to be used from the right arm with arterial entry from the radial artery. Also provided are methods of inserting the catheters into a right or left coronary artery of a patient using a transradial approach, and the use of the catheters in coronary catheterization procedure to selectively deliver a dye material, medical tool or other therapeutic device to the coronary artery of interest.

The radial catheters of the invention have a proximal end, a shaped distal end that is configured for placement in or near the right or left coronary artery, and an extended and relatively straight body portion therein between. The length of the catheter is sufficient to allow advancement of the distal end portion of the catheter into the aorta and the insertion of the tip into the ostium of the selected coronary artery using a transradial approach. The preformed distal end of the catheters includes two curved portions, or bends, that are sufficiently angled such that when the catheter is advanced into the aorta, the tip of the catheter can be engaged in the ostium of the selected coronary artery and maintained therein against counterforces that tend to displace the tip from the artery.

The distal end of the catheters includes a first curved portion, or segment, that defines a first angle and is disposed distally of the elongate body portion of the catheter, a second curved portion that defines a second angle, a straight portion that is disposed between the first and second curved portions, and a tip portion with a tip that is disposed distally of the second curved portion. The second curved portion of the right radial catheter is angled toward the first curved portion, giving the catheter a "J"-shaped appearance. The left radial catheter is "U"-shaped with the second curved portion of the distal end curved away from the first curved portion.

In use, the distal end of the radial catheters is inserted into the radial artery at the wrist or brachial artery in the arm, and advanced into the aorta via the innomirnate artery through the aortic arch and into the ascending aorta. The curvature of the distal end of the right radial catheter is such that when the first curved portion is placed against the medial wall of the ascending aorta, the straight portion and the tip portion are oriented toward the opposing lateral wall of the aorta and the right coronary artery, and the tip is placed in or near the coronary ostium. In the right radial catheter, it is preferred that the angle of the first curved portion is sufficient to position the elongate body portion and the straight portion of the distal end relative to each other at an about 40–60° angle, and the second angle is sufficient to position the straight portion of the distal end relative to the tip portion at an about 80–110° angle.

The left radial catheter of the invention is configured so that when the first curved portion is positioned against the medial wall of the ascending aorta, the second curved portion is directed toward and rests against the opposing lateral wall of the aorta so that the approach to the left coronary artery is from the contra-lateral wall, and the tip is placed in or near the coronary ostium. This configuration and contact of the curved portions of the distal end with the aortic wall provides resistance against forces that tend to flex the catheter tip out of the artery during use. Preferably, the first angle of the distal end portion of the left radial catheter is sufficient to position the elongate body portion of the catheter and the straight portion of the distal end at an about 20–40° angle relative to each other, and the second angle is sufficient to position the straight portion and the tip portion of the distal end relative to each other at an about 135–155° angle.

The present transradial coronary catheters provide a stable and reliable device for performing transradial coronary intervention procedures, and eliminate the need to conduct such procedures using a femoral or brachial catheterization approach. Advantageously, the shapes of the present radial catheters provide a catheter in which engagement of the tip with the selected coronary artery can be maintained against counterforces that tend to dislodge and cause the tip to back out of the artery, such as those that arise when advancing a tool through the catheter into the artery. The configuration of the distal end of the catheters, including the angles, or bends, of the curved portions, the placement and contact of one or both of the curved portions with the aortic wall, and the biasing force of the bends, cooperate to maintain the catheter tip within the coronary artery, and provide a secure and dependable instrument for conducting coronary diagnosis and treatment procedures. The stiffness of the material used to construct the catheter can also contribute to maintaining the catheter tip in the artery by varying the flexibility of the bends. The distal end of the radial catheters can also be easily positioned in the desired location within the aorta with minimal manual manipulation.

BRIEF DESCRIPTION OF THE DRAWINGS

Throughout the following views, reference numerals will be used in the drawings, and the same reference numerals will be used throughout the several views and in the description to indicate same or like parts of the invention.

DETAILED DESCRIPTION OF THE INVENTION

Figure 3:
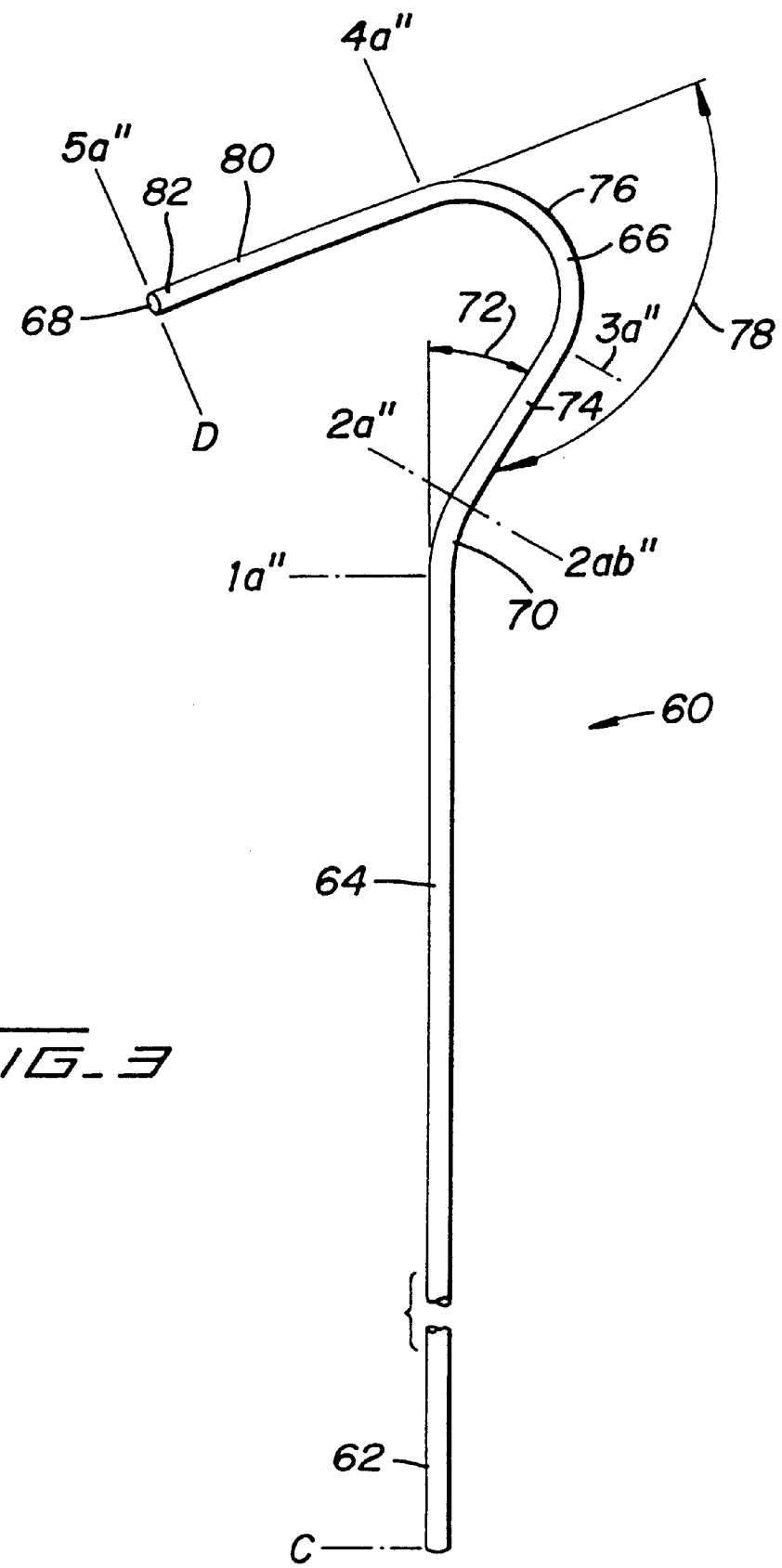
FIG. 3 is a perspective view of an embodiment of a left radial coronary catheter according to the invention.
Figure 4:
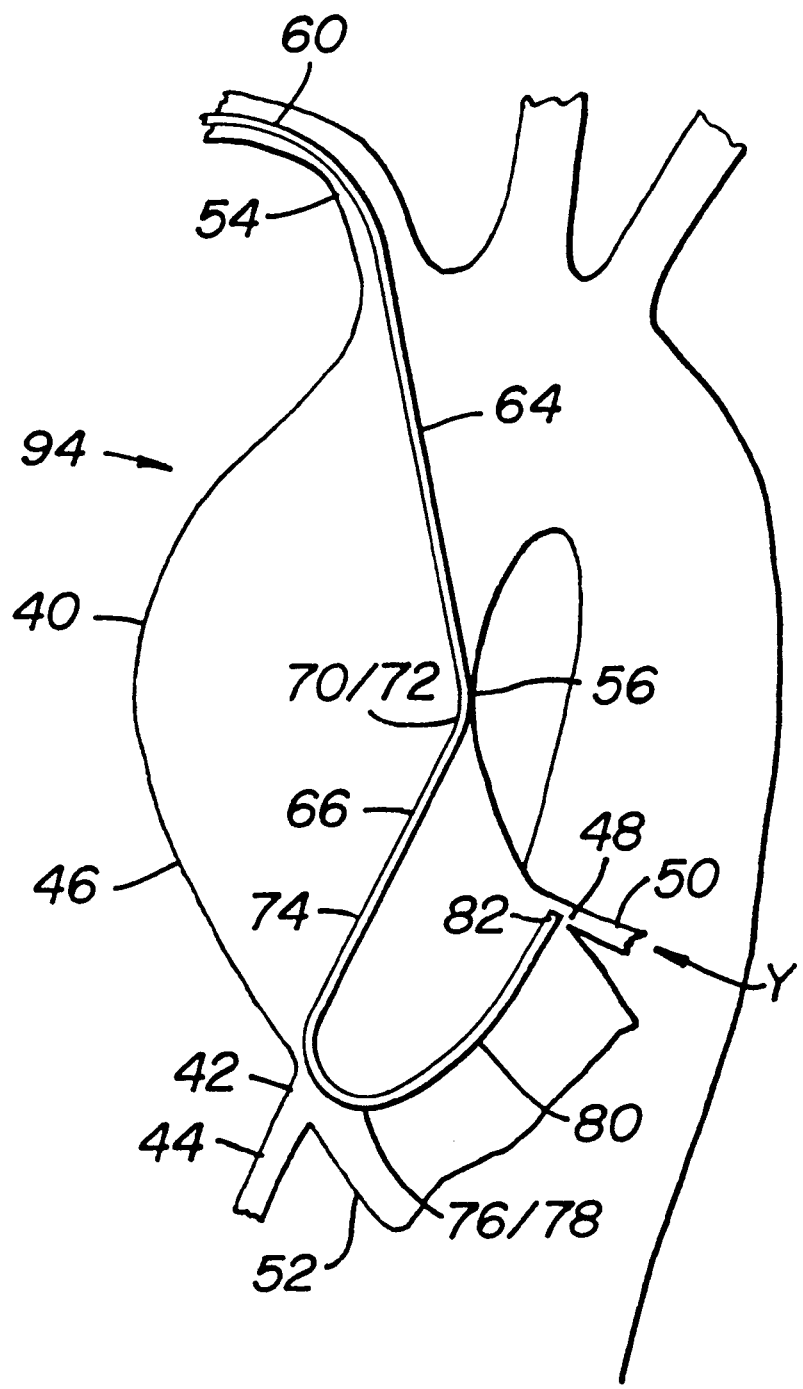
FIG. 4 is an illustration of the left radial coronary catheter of FIG. 3 in place in the aorta of a patient.

The invention will be better understood and its advantages appreciated from the following description. Referring now to the drawings, an embodiment of a right radial coronary catheter 10 according to the invention is shown in FIGS. 1 and 2, and a left radial coronary catheter 60 is shown in FIGS. 3 and 4.

Right Radial Catheter

Figure 1:
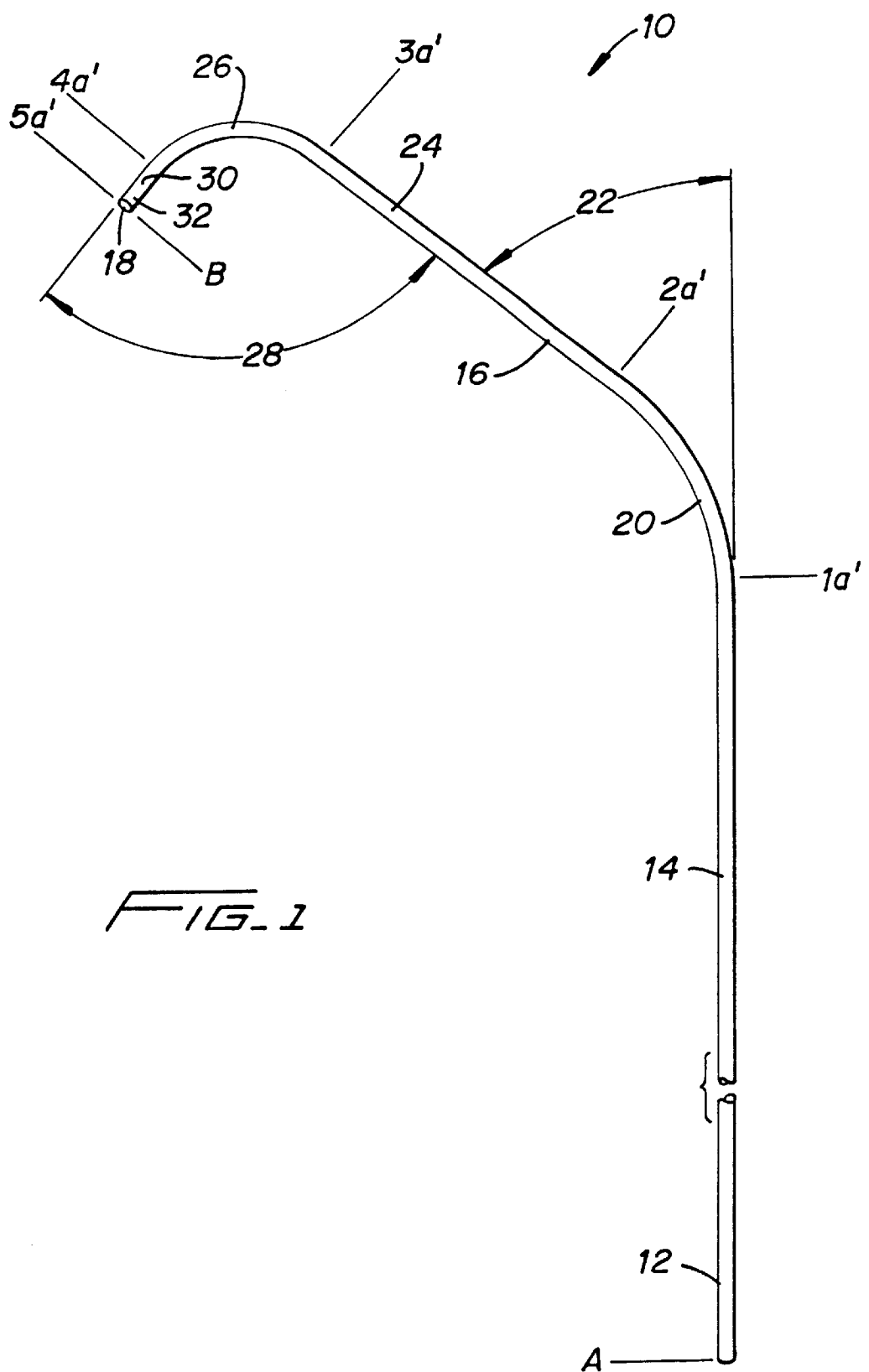
FIG. 1 is a perspective view of an embodiment of a right radial coronary catheter according to the invention.

As depicted in FIG. 1, the right radial catheter 10 is an elongate, tubular member that includes a proximal end 12, a relatively straight body portion 14, a distal end portion 16 that is relatively "J"-shaped, and a central bore 18 extending therethrough. The distal end 16 includes a first curved portion, or proximal curved segment, 20 that defines a first angle 22, a straight portion 24, a second curved portion, or distal curved segment, 26 that defines a second angle 28, a tip portion 30, and a tip 32.

Figure 2:
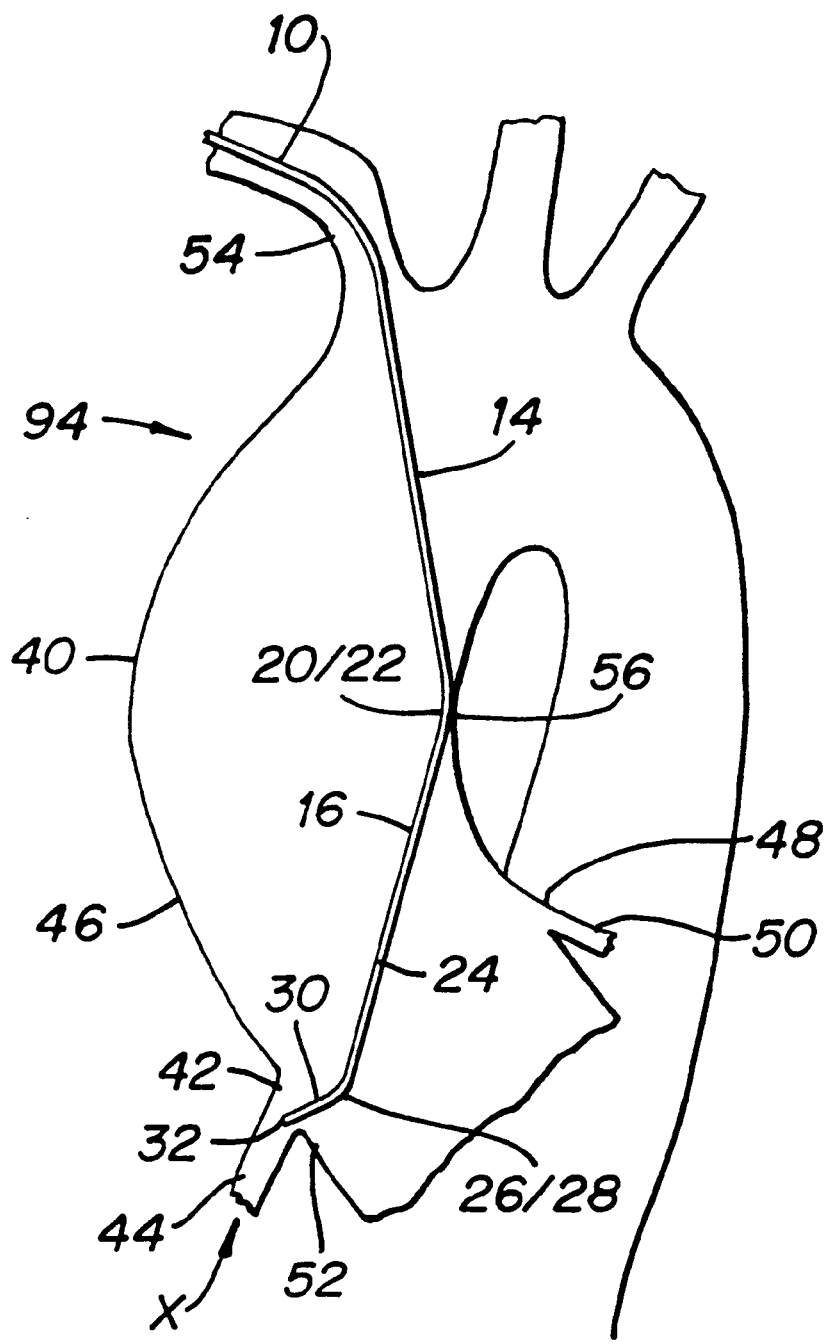
FIG. 2 is an illustration of the right radial coronary catheter of FIG. 1 in place in the aorta of a patient.

The length of the catheter 10 extending from the proximal end 12 to the tip 32, shown as the distance from "A" to "B", is sufficient to enable insertion of the tip 32 into the ascending aorta 40 and the ostium 42 of the right coronary artery 44 using a transradial catheterization approach (FIG. 2). Preferably, the catheter 10 has a length A–B of about 110–125 cm, preferably about 115 cm.

As shown in FIG. 2, the distal end 16 is shaped to position the tip portion 30 in proximity to the right coronary artery 44 and engage and securely maintain the tip 32 within the coronary ostium 42 during a coronary procedure. The first or proximal curved portion 20 of the catheter 10 serves to direct the catheter 10 to the lateral wall 46 of the ascending aorta 40 for selective engagement of the right coronary artery 44. The second or distal curved portion 26 allows for coaxial engagement of the coronary artery 44.

It is preferred that the first angle 22 of the distal end portion 16 is curved at an about 40–60° angle, more preferably at an about 45–55° angle, more preferably at an about 50° angle. The second curved portion 26 is curved toward the first curved portion 20, preferably at an about 80–110° angle, more preferably at an about 85–100° angle, more preferably at an about 90° angle. It is further preferred that the length 1a'–2a' of the first curved portion 20 is about 30–40 mm, more preferably about 33–37 mm; the length 2a'–3a' of the straight portion 24 is about 40–60 mm, preferably about 45–55 mm; the length 3a'–4a' of the second curved portion 26 is about 18–26 mm, more preferably about 20–24 mm; and the length 4a'–5a' of the tip portion 30 is about 4–8 mm, preferably about 5–7 mm.

The catheter can be dimensioned to accommodate varying sizes of patients. A preferred embodiment of a standard (4.0) right radial catheter 10 has a distal end portion 16 with an about 35 mm long first curved portion 20 at an about 50° angle, an about 50 mm straight portion 24, an about 22 mm long second curved portion 26 at an about 90° angle, and an about 6 mm tip portion. To accommodate a patient having a wider or narrower aorta, as measured by a radioimaging procedure, the lengths and/or angles of the segments of the distal end portion 16, for example, the length of the straight portion 24 and the proximal angle (first curved portion) 20, can be adjusted accordingly.

Left Radial Catheter

FIG. 3 depicts an embodiment of a left radial catheter 60 according to the invention. The left radial catheter 60 includes a proximal end 62, a straight body portion 64, and a distal end portion 66. A central bore 68 extends therethrough. The distal end 66 is formed in the shape of a "U" and includes a first curved portion, or proximal curved segment, 70 that defines a first angle 72, a straight portion 74, a second curved portion, or distal curved segment, 76 that defines a second angle 78, a tip portion 80, and a tip 82. The second curved portion 76 curves away from the first curved portion 70.

As depicted in FIG. 3, the length of the catheter 60 is measured as the distance "C" to "D". The length C–D is sufficient for placement of the tip 82 into the ostium 48 of the left coronary artery 50 by a transradial catheterization procedure. Preferably the length C–D of the catheter 60 is about 110–125 cm, preferably about 115 cm.

The shape and dimensions of the distal end 66 are sufficient to enable engaging and maintaining the catheter tip 82 coaxially in the ostium 48 of the left coronary artery 50 during use in a coronary procedure, as shown in FIG. 4. The first or proximal curved portion 70 serves to direct the catheter to the lateral wall 46 of the ascending aorta 40 at about the level of the coronary cusps 52 so that the approach to the left coronary artery 50 is from the contra-lateral wall 46 of the aorta. This enhances the ability of the catheter 60 to engage the coronary artery 50 and provide a secure base for coronary interventional procedures. The second or distal curved portion 76 then directs the catheter tip 82 to the left coronary artery 50 for selective engagement.

Preferably, the first or proximal curved portion 70 provides a first angle 72 that is about 20–40°, more preferably about 25–35°, more preferably about 30°, and the second or distal curved portion 76 provides a second angle 78 that is about 130–150°, more preferably about 135–145°, more preferably about 140°. The first curved portion (arc) 70 has a preferred length 1a"–2a" of about 6–11 mm, more preferably about 7–10 mm, more preferably about 8–9 mm; the straight portion 74 has a preferred length 2ab"–3a" of about 16–24 mm, more preferably about 18–22 mm; the second curved portion (arc) 76 has a preferred length 3a"–4a" of about 23–32 mm, more preferably about 25–29 mm; and the tip portion 80 has a preferred length 4a"–5a" of about 23–41 mm, preferably about 25–35 mm.

In a preferred embodiment of the left radial catheter, the first curved portion 70 has an angle 72 of about 30° and a length 1a"–2a" of about 8.4 mm, the straight portion has a length 2ab"–3a" of about 20 mm, and the second curved portion has an angle 78 of about 141° and a length 3a"–4a" of about 27.5 mm, with a variable length 4a"–5a" for the tip portion. For example, a standard (4.0) left radial catheter preferably has a tip portion of about 28–33 mm, preferably about 29–32 mm, preferably about 30.5 mm; a 3.5 catheter has an about 23–28 mm tip portion, preferably about 24–27 mm, preferably about 25.4 mm; and a 4.5 catheter has an about 33–38 mm tip portion, preferably about 34–37 mm, preferably about 35.6 mm.

To accommodate individual patients, it is preferred that the length of the tip portion 80 and/or the angle 78 are adjusted according to the size of the ascending aorta of the patient, which can be determined by imaging and visually observing the aorta, of the patient.

Use of the Right and Left Radical Catheters

Figure 5:
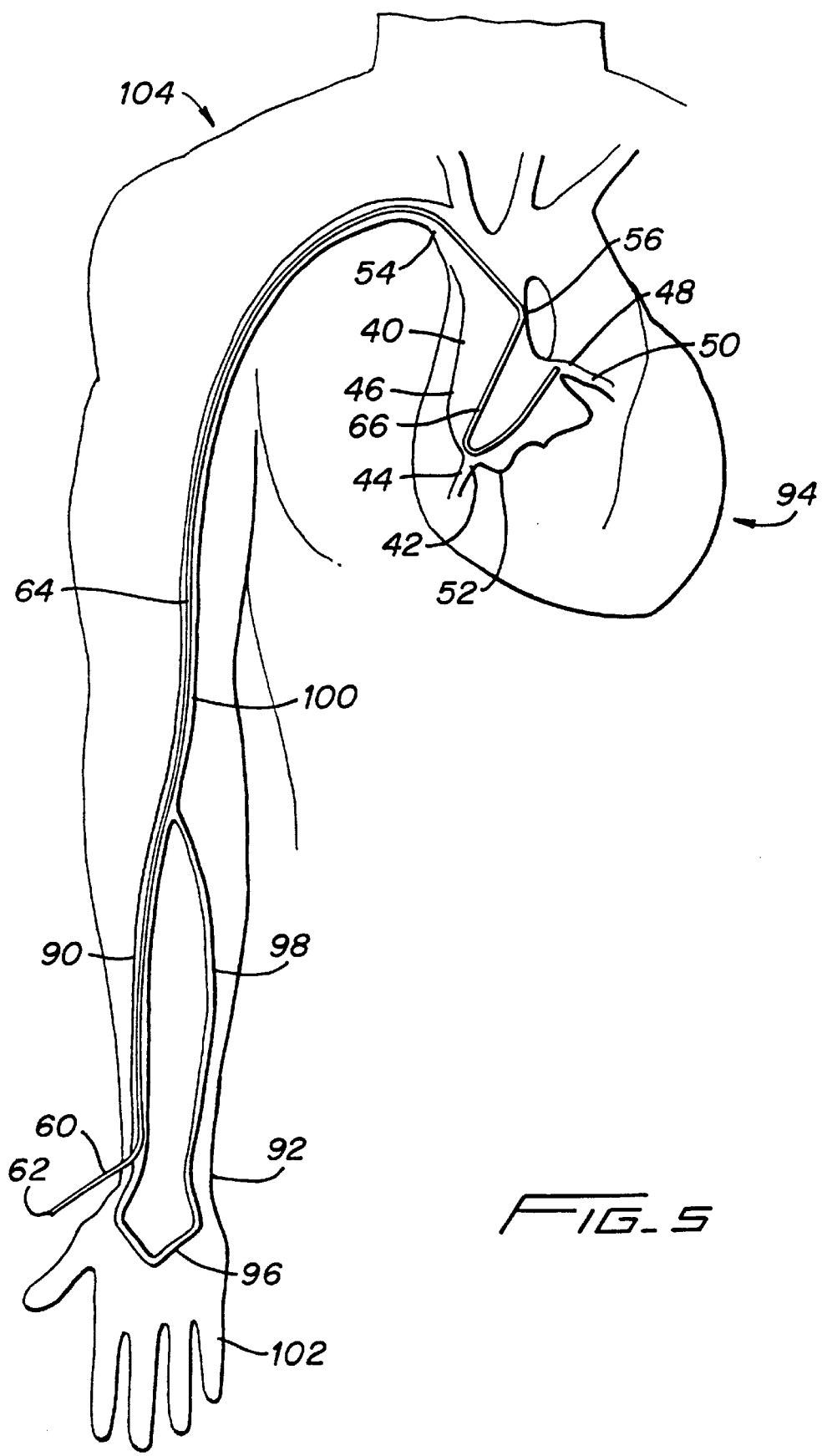
FIG. 5 is an illustration of a transradial approach using the left radial coronary catheter of FIG. 3.

The right and left radial catheters 10, 60 can be used in a conventional transradial catheterization procedure in which the catheter is inserted into the radial artery 90 of the wrist 92 and advanced into the ascending aorta 40. Such a procedure using a left radial catheter 60 according to the invention is illustrated in FIG. 5. The radial artery 90 is superficially located and can be easily accessed in most patients to facilitate arterial cannulation. Also, the radial artery 90 is one of two small arteries in the wrist 92 that communicate through the palmar arch 96. Due to the collateral flow to the hand through the ulnar artery 98 and the palmar arch 96, patients with intact ulnar flow experience no significant clinical sequelae due to the occlusion of the radial artery 90. This is a distinct advantage over brachial catheterizations in which the catheter inserted into the brachial artery 100 of the arm tends to cut off of blood flow into the lower arm, wrist and hand. In addition, the radial artery 90 is sufficiently located away from significant veins or nerves to avoid damage from the insertion of the catheter into the artery.

The superficial location of the radial artery 90 also facilitates easy control of bleeding after the procedure so there is decreased risk of bleeding complications. After a transradial procedure using the present catheters, pressure need be applied at the incision at the wrist for only about 15 minutes, a true benefit to patient comfort since they are able to ambulate almost immediately after the procedure. By comparison, about 4–6 hours of immobilization is required after a femoral catheterization, and about 1–2 hours rest period is needed after a brachial catheterization, to ensure that bleeding from the incisional wound is stopped.

It is understood, however, that the right and left catheters 10, 60 of the invention can also be effectively used in a brachial catheterization by advancing the distal end portion 16, 66 of the catheter 10, 60 through a surgical incision in the brachial artery 100 in the arm, and then advancing the catheter into the aorta 40. Placement of the catheter 10, 60 would then be in accordance with the placement using a radial approach as described herein.

In a transradial approach, a puncture is made into the radial artery 90 of the right hand 102 of the patient 104, and a sheath (not shown) is inserted through the puncture into the artery 90. The tip 32, 82 of the catheter 10, 60, respectively, is then advanced into the sheath and advanced into the radial artery 90. The distal end 16, 66 of the catheter 10, 60 is then advanced through the radial artery 90 and into the brachial artery 100. The tip 32, 82 is then advanced to the ascending aorta.

To aid in the advancement of the catheters 10, 60 through the radial artery 90 into the ascending aorta 40 of the heart 94, a flexible guidewire, as known and used in the art (not shown), can be inserted into the bore 18, 68 of the catheter 10, 60 to straighten the curved portions of the distal end 16, 66. Once the distal end portion 16, 66 is advanced into the ascending aorta 40, the guidewire can then be removed from the catheter 10, 60.

The catheters 10, 60 are manufactured from a material that can be resiliently deformed to enable passage of the catheter through the radial artery and aortic arch and to the desired position within the ascending aorta,. Preferably, the catheter is made of a radiopaque material so that it can be viewed within the body, for example by X-ray or other similar technique. Such materials are known and used in the art, as for example, the material described in U.S. Pat. Nos. 5,403,292 (Ju) and U.S. Pat. No. 5,599,325 (Ju et al.).

Placement of the catheters 10, 60, is shown in FIGS. 2 and 4, respectively. The distal end portion 16, 66 of the catheter 10, 60 is advanced via the innominate artery 54 into the ascending aorta 40. The curved portions of the distal end 16, 66 cooperate with the aorta 40 to place the tip 32, 82 of the catheter 10, 60 into proximity with the coronary ostium 42, 48 as the distal end portion 16, 66 is advanced into the ascending aorta 40. As the catheter is advanced into the aorta, the first curved portion 20, 70 of the distal end 16, 66 of the catheters 10, 60, is placed against the medial wall 56 of the ascending aorta 40 at about the superior aspect, and the straight portion 24, 74 and the second curved portion 26, 76 are oriented toward the opposing lateral wall 46 of the aorta 40. Minimal manual manipulation is needed to position the catheter. Placement of the catheter within the aorta can be observed, for example, by X-ray.

With the right radial catheter 10, as shown in FIG. 2, the tip portion 30 is positioned in proximity of the right coronary artery 44. The tip 32 can then be engaged coaxially in the coronary ostium 42. The contact of the first curved portion 20 with the medial aortic wall 56, and the biasing effect of the angles, or bends, 22, 28, cooperate to engage and maintain the tip 32 of the right radial catheter 10 in the ostium 42 of the right coronary artery 44 when a counterforce, shown as arrow "X", is directed from the artery 44 toward the curved portion 26.

Referring now to FIG. 4 showing the placement of the left radial catheter 60, with the first curved portion 70 positioned against the medial aortic wall 56, the second curved portion 76 is placed so that it rests against the opposing lateral wall 46 at about the level of the coronary cusp 52. By positioning the second curved portion 76 in contact with the lateral wall 46, the approach to the left coronary artery 50 is from the contra-lateral wall 46. The position of the second curved portion 76 orients the tip portion 80 toward the left coronary artery 50, and the tip 82 can then be coaxially engaged in the coronary ostium 48. The bends, or angles, 72, 78 of the distal end 615 provide a spring-like pressure that biases the first curved portion 70 against the medial aortic wall 56, the second curved portion 76 against the opposing lateral wall 46, and the tip 82 into the ostium 48 of the left coronary artery 50. The contact of the curved portions with the aortic wall 46, 56 and the biasing effect of the bends 72, 78 cooperate to maintain the tip 82 within the ostium 48 of the artery 50 against a counterforce, shown as arrow "Y," directed from the artery 50 toward the second curved portion 76.

In performing a transradial coronary procedure, it is desirable that an initial evaluation be conducted in which the patient undergoes an assessment of ulnar flow. A patient should be excluded from a transradial coronary approach if they do not have a palpable ulnar artery 98 or had an abnormal Allen's test (E. V. Allen, *Am. J. Med. Sci.* 178:237 (1929)). Briefly, a gross test of ulnar patency can be conducted as a simple, bedside maneuver in which the radial and ulnar arteries, 90, 98, respectively, are simultaneously occluded while the patient makes a fist. When the hand is opened it will appear blanched, and release of the ulnar artery 98 should result in noticeable return of color to the palm within 10–15 seconds.

In preparing for the procedure, it is preferred that the patient is sedated and comfortably positioned on the catheterization table. The patient's arm is preferably abducted at an about 70° angle on an armboard for initial sheath insertion. A movable arm board is preferred in that it allows the arm to be positioned at the patient's side during the procedure. A roll of sterile towels can be used to support the wrist in a hyperextended position. The anterior surface of the distal forearm and proximal hand are prepped in a sterile fashion. A 2% lidocaine solution or other like substance can be applied as a local anesthetic to infiltrate the skin over the radial artery in order to reduce spasm and improve patient comfort. Preferably, a topical anesthetic cream such as EMLA® cream (Astra Pharmaceutical Products, Westborough, Mass.) is used in order to reduce the amount of lidocaine that is used in the procedure since large amounts of lidocaine can obliterate the pulse and make cannulation difficult.

Arterial puncture can be achieved with a commercial radial artery catheterization set such as that distributed under the trademark Arrows by Arrow® International, Inc., Reading, Pa. The integrated guidewire within the Arrow ® catheterization set allows cannulation of the radial artery 90 with minimal manipulation. The radial artery 90 is preferably cannulated using an 18 or 20 gauge 1.75-inch catheter over a 22 gauge thin-walled needle with a guidewire.

For insertion of the catheter into the radial artery 90, it is preferred that a short sheath of about 11 cm is used, preferably in combination with a medicament to reduce discomfort. About 2,000–5,000 units of heparin can be introduced into a side port of the sheath to prevent thrombosis.

Preferably, a vasodilating agent is administered intra-arterially through the sheath in order to minimize spasm of the radial artery during the transradial procedure. Significant radial artery spasm may not only limit catheter manipulation and increase the complexity of the procedure, but spasms may also result in significant patient discomfort. Examples of useful vasodilating agents that do not produce hypotensicin, bradycardia, or other unwanted side effects, include diltiazem, papaverine, adenosine, with verapamil being preferred. Preferably, the vasodilator is administered at a dose of about 1–2 milligrams, although up to about 5 milligrams can be used during the course of a procedure without side effects.

An appropriately sized right or left radial catheter 10, 60 according to the invention is then selected for the coronary angiography and/or intervention procedure, according to the size of the patient.

The present right and left radial catheters 10, 60 can be used in any conventional coronary diagnostic or treatment procedure. For example, the catheters 10, 60 can be utilized to image an occlusion of a coronary artery using a coronary angiography (arteriography) technique in which a radio-paque dye is injected through the bore of the catheter and into the selected artery. The injected dye can then be imaged by X-ray or a fluoroscope to map the movement of the dye through the artery, or to show the location of the tip in the artery.

The catheters of the invention can also be used in an angioplasty procedure to introduce a device or interventional tool or equipment to a desired site to perform a diagnostic or interventional procedure. In such procedures, the device would be advanced through the bore 18, 68 of the catheter 10, 60 and then into the coronary artery. Such devices are known and used in the art, and include for example, a catheter that is tipped with a miniature, deflated balloon that can be maneuvered through a blockage in the artery and inflated to flatten plaque and widen the passageway through the artery, a sensor that is operable for visualizing the lumen of the artery, a cutting tool that is operable to remove fatty deposits or tissue, or a device such as a stent.

At the end of the procedure, the catheter 10, 60 and then the sheath are removed. Prior to sheath removal, it is preferred that a vasodilating agent is administered through the sheath to minimize spasm of the radial artery and to reduce the number of radial artery occlusions. Preferably, about 1 milligram of verapamil or other like vasodilator is administered. After removal of the sheath, manual pressure is applied on the puncture site for about 10–15 minutes to attain hemostasis. A small pressure dressing or sterile adhesive dressing can then be placed onto the puncture site prior to discharge of the patient. Discharge of the patient to the home is typically about 1–2 hours following sheath removal.

In the immediate post-catheterization period after the sheath is removed, excessive movement of the wrist should be avoided for several hours. A clinical examination or Doppler ultrasound evaluation of the cannulated artery can then be performed to check for occlusion or stenosis.

The transradial approach has several advantages compared to the femoral and brachial routes for cardiac catheterization. For example, the radial artery is easily accessible in most patients and is not located near significant veins or nerves. Arterial cannulation is facilitated by the superficial location of the radial artery. Occlusion of the radial artery also has the advantage of no significant clinical sequelae in patients with a normal Allen's test due to the collateral flow to the hand through the ulnar artery and the palmar arch. After the procedure, the superficial location of the radial artery is also important in the superior control of the artery and decreased risk of bleeding complications. In addition, patient comfort is enhanced by the ability to ambulate immediately after the procedure.

The invention has been described by reference to detailed examples and methodologies. These examples are not meant to limit the scope of the invention. Variation within the concepts of the invention are apparent to those skilled in the art. The disclosures of the cited references throughout the application are incorporated by reference herein.

What is claimed is:

1. A catheter for use in a right coronary artery of a patient, comprising:

an elongated tubular member having a proximal end, a distal end portion and a body portion therein between, and a central bore therethrough;

the distal end portion having a first curved portion defining a first angle and disposed distally of the body portion, a second curved portion defining a second angle, a straight portion disposed between the first and second curved portions, and a tip portion having a tip and disposed distally of the second curved portion;

wherein when inserted into a cardiovascular system and the first curved portion is positioned against the medial wall of the ascending aorta, the first and second angles are sufficient to direct the straight portion and the tip portion toward the lateral wall of the aorta for engaging the tip portion coaxially within the ostium of the right coronary artery.

2. The catheter according to claim 1, wherein the angle and contact of the first curved portion with the aortic wall are effective to maintain the tip in the artery upon the application of a counterforce to displace the tip from the ostium directed from the artery toward the second curved portion of the catheter.

3. The catheter according to claim 1, wherein the first angle is about 40–60°, and the second angle curves toward the first curved portion and is about 80–110°.

4. The catheter according to claim 1, wherein the body portion and the straight portion of the distal end are disposed relative to each other at an about 45–55° angle, the straight portion and the tip portion are disposed relative to each other at an about 85–100° angle, and the second curved portion curves toward the first curved portion.

5. The catheter according to claim 1, wherein the dimensions and configuration of the catheter enable insertion of the catheter tip into the right coronary artery by means of a radial or brachial artery approach.

6. The catheter according to claim 1, wherein the body portion of the catheter has a length sufficient for inserting the tip into the artery by a transradial approach.

7. The catheter according to claim 1, wherein the distal end portion is configured such that when the catheter is inserted into the cardiovascular system, the first curved portion is positioned against the medial aortic wall at about the superior aspect of the ascending aorta.

8. The catheter according to claim 1, wherein the first curved portion is about 30–40 mm in length, the straight portion is about 40–60 mm in length, the second curved portion is about 20–24 mm in length, and the tip portion is about 4–8 mm in length.

9. The catheter according to claim 1, wherein the straight portion is about 45–55 mm in length, and the tip portion is about 5–7 mm in length.

10. A catheter for use in a right coronary artery of a patient, comprising:

an elongated tubular member having a proximal end, a distal end portion, a body portion therein between, and a central bore therethrough;

the distal end portion having a first curved portion disposed distally of the body portion, a second curved portion, and a relatively straight portion between the first and second curved portions, and a tip portion with a tip disposed distally of the second curved portion; the first curved portion defining an about 40–60° angle, and the second curved portion defining an about 80–110° angle;

wherein when inserted into a cardiovascular system and the first curved portion is positioned against the medial wall of the ascending aorta, the angle of the first curved portion is sufficient to direct the straight portion and the tip portion toward the lateral wall of the aorta, and the angle of the second curved portion is sufficient to direct the tip portion toward the right coronary artery for coaxially engaging the tip within the ostium of the artery.

11. A catheter for use in a right coronary artery of a patient, comprising:

an elongated tubular member having a proximal end, a distal end portion and a body portion therein between, and a central bore therethrough;

the distal end portion having a first curved portion disposed distally of the body portion, a second curved portion, and a relatively straight portion between the first and second curved portions, and a tip portion disposed distally of the second curved portion and having a tip;

the first curved portion about 30–40 mm in length and defining an about 40–60° angle, the second curved portion about 20–24 mm in length and defining an about 80–110° angle that curves toward the first curved portion; the straight portion about 40–60 mm in length; and the tip portion about 4–8 mm in length;

wherein the dimensions and configuration of the catheter are sufficient to enable insertion of the catheter tip into the right coronary artery by means of a radial or brachial artery approach; and the angles and contact of the distal end of the catheter are sufficient to engage the tip coaxially within the ostium of the right coronary artery when the distal end of the catheter is inserted into a cardiovascular system and the first curved portion is positioned against the medial wall of the ascending aorta.

12. A method of inserting a catheter into a right coronary artery of a patient, comprising:

providing a catheter according to claim 1;

advancing the distal end portion of the catheter through the aortic arch into the ascending aorta; and positioning the distal end portion in the aorta with the first curved portion in contact with the medial aortic wall near the superior aspect of the ascending aorta, the second end portion in proximity of the right coronary artery, and the tip coaxially engaged in the ostium of the artery.

13. The method according to claim 12, further comprising:

inserting the distal end portion of the catheter into the right radial artery to advance the catheter into the aorta.

14. The method according to claim 12, further comprising:

inserting the distal end portion of the catheter into the brachial artery to advance the catheter into the aorta.

15. The method according to claim 12, further comprising:

inserting a flexible guidewire into the bore of the catheter to straighten the curved portions of the distal end; and removing the guidewire from the catheter after the distal end portion is advanced into the ascending aorta.

16. The method according to claim 12, further comprising:

injecting a dye through the bore of the catheter into the artery; and imaging the dye to show the location of the tip.

17. The method according to claim 12, further comprising:

injecting a dye through the bore of the catheter into the artery to image the right coronary artery.

18. The method according to claim 12, further comprising:

advancing a device operable for visualizing the artery, through the bore of the catheter into the artery.

19. The method according to claim 12, further comprising:

advancing an interventional device through the bore of the catheter into the artery.

\* \* \* \* \*